United States Patent
Wang et al.

(10) Patent No.: US 6,689,900 B2
(45) Date of Patent: Feb. 10, 2004

(54) FLUORINATED CROSSLINKER AND COMPOSITION

(75) Inventors: Fang Wang, Tewksbury, MA (US); Baopei Xu, Wakefield, MA (US); Indira S. Pottebaum, Boston, MA (US); Chuck C. Xu, Tewksbury, MA (US)

(73) Assignees: E. I. du Pont de Nemours and Company, Wilmington, DE (US); Telephotonics Incorporated, Wilmington, DE (US)

( * ) Notice: Subject to any disclaimer, the term of this patent is extended or adjusted under 35 U.S.C. 154(b) by 0 days.

(21) Appl. No.: 10/062,852

(22) Filed: Jan. 31, 2002

(65) Prior Publication Data

US 2002/0111518 A1 Aug. 15, 2002

Related U.S. Application Data

(60) Provisional application No. 60/267,532, filed on Feb. 9, 2001, and provisional application No. 60/267,541, filed on Feb. 9, 2001.

(51) Int. Cl.$^7$ .............................................. C07C 69/66
(52) U.S. Cl. ....................................................... 560/182
(58) Field of Search .......................................... 560/182

(56) References Cited

U.S. PATENT DOCUMENTS

| | | | |
|---|---|---|---|
| 3,651,073 A | * | 3/1972 | Khan et al. ................ 260/297 |
| 4,508,916 A | * | 4/1985 | Newell et al. ............... 556/420 |
| 4,511,209 A | | 4/1985 | Skutnik |
| 4,877,717 A | | 10/1989 | Suzuki et al. |
| 4,914,171 A | | 4/1990 | Zweig |
| 5,024,507 A | | 6/1991 | Minns et al. |
| 5,062,680 A | | 11/1991 | Imamura et al. |
| 5,223,593 A | | 6/1993 | McAllister et al. |
| 5,822,489 A | | 10/1998 | Hale |
| 6,133,472 A | | 10/2000 | Nalewajek et al. |
| 6,162,579 A | | 12/2000 | Stengel et al. |

FOREIGN PATENT DOCUMENTS

EP 0 333 464 9/1989

OTHER PUBLICATIONS

"Low Surface Energy Coatings on Substrates Prepared Via Radiation Curing." Pacansky et al. *Elsevier Science S.A..* 1990. pp. 79–87.

"Properties of UV–curable coatings containing fluorinated acrylic structures." Bongiovanni et al. *Elsevier Science S.A.* 1999. pp. 70–78.

* cited by examiner

*Primary Examiner*—Alan L. Rotman
*Assistant Examiner*—Hector M Reyes

(57) ABSTRACT

Fluorinated multifunctional alcohols containing at least 3 primary hydroxyl groups are disclosed. Such alcohols allow for easy synthesis of multifunctional crosslinkers such as acrylates, epoxies and vinyl ethers. The multifunctional crosslinkers are used in fluorinated optical coating and waveguide compositions to increase curing speed and crosslinking density.

19 Claims, No Drawings

FLUORINATED CROSSLINKER AND COMPOSITION

PRIORITY INFORMATION

This application claims priority from provisional application Ser. Nos. 60/267,532 and 60/267,541 both of which were filed Feb. 9, 2001.

BACKGROUND OF THE INVENTION

The invention is directed to a class of fluorinated multifunctional alcohols and their derivatives such as acrylates and methacrylates, collectively referred to herein as acrylates, epoxies and vinyl ethers. The acrylates, epoxies and vinyl ethers are used as crosslinkers in compositions for optical coatings and waveguide devices.

Prior art references have disclosed that fluorine-containing polymers may be used for coating applications. See, for example, A. A. Wall, Fluoropolymers, Wiley-Interscience, 1972, and T. Deisenroth, Proc. Fluorine in Coatings II, Munich, 1997. The fluorinated polymers offer unique properties such as excellent chemical and thermal stability, good weathering and humidity resistance, low surface tension, low refractive index, and low absorption in the electromagnetic spectral region from 1300 to 1610 nm. The 1300–1610 nm region of the electromagnetic spectrum is particularly useful for fiber optic telecommunication networks. For example fluoropolymers have been used to coat optical fibers as well as to fabricate optical waveguides.

It is well known in the art that actinic radiation such as UV light permits fast curing. UV curable compositions containing fluorinated monomers, oligomers and polymers have been widely reported. See, for example, U.S. Pat. Nos. 4,508,916; 4,511,209; 4,914,171; 5,024,507; 5,062,680; 5,223,593; 5,822,489; 6,133,472; European patent No. 333,464A1; and publications including J. Pacansky, Progress in Organic Coatings, 18 (1990) 79 and R. Bongiovanni, Progress in Organic Coatings, 36 (1999) 70; all of which are herein incorporated by reference. These compositions comprise fluorinated mono- or multi-functional acrylates or vinyl ethers and at least one photoinitiator.

Most of the fluorinated acrylates disclosed in the prior art contain one or two acrylate groups per molecule. However, to achieve fast cure and high crosslinking density it is desirable that multifunctional crosslinkers having at least 3 functional groups per molecule are added to the formulations. Multifunctional hydrocarbon monomers such as acrylates, vinyl ethers and epoxies have been widely used as crosslinkers but their poor solubility in highly fluorinated monomers and polymers limits their applications in fluorocoatings. Ausimont USA of Thorofare, N.J. provides Fluorolink T and T10, which have four hydroxyl groups per molecule. However two of the four hydroxyl groups are attached to secondary carbon atoms. As is well known to those skilled in the art, due to steric hindrance, it is very difficult to fully convert the secondary hydroxyl groups to other functional groups such as acrylates, epoxies, and vinyl ethers, especially in the presence of primary hydroxyl groups. Incomplete conversion of hydroxyl groups makes it less suitable for applications requiring low moisture uptake and low optical absorption in the 1300–1600 nm wavelength regions.

Therefore there is a need for a fluorinated alcohol having at least 3 primary alcohol groups per molecule. Such alcohol is suitable to being converted to crosslinkers containing at least 3 functional groups selected from the group consisting of acrylate, epoxy and vinyl ether. The crosslinkers may be used in fluorinated optical coating and waveguide compositions.

SUMMARY OF THE INVENTION

A fluorinated multifunctional alcohol having at least 3 primary hydroxyl groups is synthesized. The alcohol is subsequently converted to multifunctional crosslinkers such as acrylates, epoxies and vinyl ethers.

One object of this invention is to provide a new fluorinated multifunctional alcohol having at least three primary hydroxyl groups.

It is another object of the invention to provide a multifunctional alcohol that is a suitable precursor to fluorinated multifunctional acrylates, epoxies, and vinyl ethers.

Another object of the invention is to provide a new fluorinated multifunctional acrylate synthesized from the fluorinated multifunctional alcohol of the present invention.

It is still another object of the invention to provide a coating composition comprising the multifunctional acrylate of the present invention.

Still another object of this invention is to provide a method for producing an optical coating comprising (I) forming a coating composition comprising at least one acrylate and at least one free radical initiator; (II) coating the composition into a film on a substrate having a substantially uniform thickness; and (III) curing the coating composition by exposure to an actinic radiation or heat, depending on the type of the initiator.

Yet still another object of this invention is to provide a waveguide device formed by patterning the coating composition of the present invention.

DETAILED DESCRIPTION OF PREFERRED EMBODIMENTS

The fluorinated multifunctional alcohol of the present invention has at least three primary hydroxyl groups. Its structure can be described using the following formula:

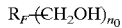

wherein $R_F$ is a fluorinated mono- or multi-valent radical such as aromatic and aliphatic esters, ethers, amides, urethanes, and mixtures thereof, and no is an integer of at least 3. Preferably the fluorine content in $R_F$ is at least 20% by weight to allow for sufficient solubility of the crosslinker in a fluorinated coating composition.

In a preferred embodiment the fluorinated multifunctional alcohol of the present invention has the following formula:

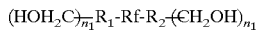

wherein Rf is a monomeric or polymeric perfluorinated alkylene, oxyalkylene, arylene, oxyarylene, and mixtures thereof; $R_1$ and $R_2$ are monomeric or polymeric multi-valent radicals such as aromatic and aliphatic esters, ethers, amides, urethanes, and mixtures thereof; and $n_1$ is an integer of at least 2, preferably from 2 to 4. Typically Rf has a molecular weight of at least 25% of the molecular weight of the alcohol to allow for sufficient solubility of the crosslinker in a fluorinated coating composition and to reduce optical absorption in the wavelength region of 1300–1600 nm.

In one preferred embodiment the fluorinated multifunctional primary alcohol, A, is synthesized from a fluorinated diol, B, and a carboxylic compound, C, containing one hydroxy-reacting group and at least two primary alcohol groups. B and C react to form an ester.

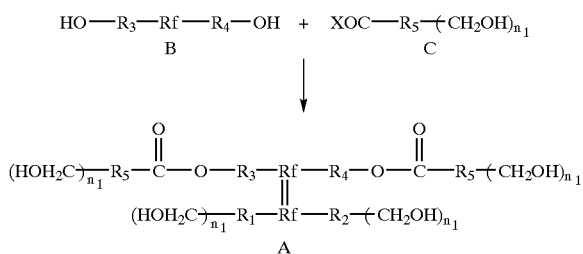

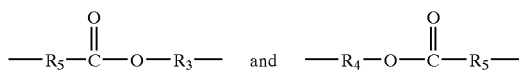

wherein Rf is a monomeric or polymeric perfluorinated alkylene, oxyalkylene, arylene, oxyarylene, and mixtures thereof; $R_3$ and $R_4$ are monomeric or polymeric divalent moieties such as alkylene, oxyalkylene, alkylene sulfide, arylene, oxyarylene, arylene sulfide, siloxane, and mixtures thereof; X stands for a hydroxyl, halide or alkoxy group, $R_5$ is an aliphatic or aromatic moiety and $n_1$ ranges from 2 to 4. In the above scheme $R_1$ and $R_2$ in A represent the following ester groups formed, respectively:

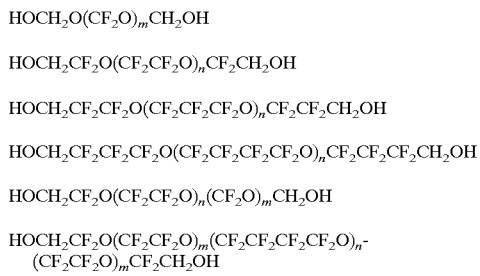

To avoid polymerization during the reaction it is preferred that the hydroxyl groups in C be protected before the reaction and then de-protected after the reaction.

Examples of suitable fluorinated diols, B, include, but are not limited to, 1H,1H,9H, 9H-perfluoro-1,9-nonanediol, 1H,2H,3H,3H-perfluorononane-1,2-diol, 1H,1H,10H,10H-perfluoro-1,10-decanediol, 1H,1H,12H,12H-perfluoro-1,12-dodecanediol, 1H,1H,16H,16H-perfluoro-1,16-hexadecanediol, 1H 1H,8H,8H-perfluorotetraethyleneglycol, fluoro-poly(alkylene) diol, ethoxylated fluoropoly(alkylene) diols, fluoropoly (oxyalkylene) diols having the following structures:

$HOCH_2O(CF_2O)_mCH_2OH$ $HOCH_2CF_2O(CF_2CF_2O)_nCF_2CH_2OH$ $HOCH_2CF_2CF_2O(CF_2CF_2CF_2O)_nCF_2CF_2CH_2OH$ $HOCH_2CF_2CF_2CF_2O(CF_2CF_2CF_2CF_2O)_nCF_2CF_2CF_2CH_2OH$ $HOCH_2CF_2O(CF_2CF_2O)_n(CF_2O)_mCH_2OH$ $HOCH_2CF_2O(CF_2CF_2O)_m(CF_2CF_2CF_2CF_2O)_n\text{-}(CF_2CF_2O)_mCF_2CH_2OH$ and $HOCH_2CF_2O(CF_2CF_2O)_m(CF_2CF_2CF_2O)_nCF_2CF_2O\text{-}(CF_2CF_2CF_2O)_n(CF_2CF_2O)_mCF_2CH_2OH$ wherein m and n are independent integers, perfluoropolyether diols and ethoxylated perfluoropolyether diols such as Fluorolink D, D10, E and E10 commnercially available from Ausimnont USA, and other variations known to those skilled in the art.

Examples of suitable compound C include but are not limited to 2,2-bis(hydroxymethyl)propionic acid, 3-hydoxyl-2,2-bis(hydroxymethyl)propionic acid, 2,2-bis(hydroxymethyl)butyric acid, 4-hydroxy-3,3-bis(hydroxymethyl)butyric acid, and 3,3-bis(hydroxymethyl) butyric acid.

In another embodiment, the fluorinated multifunctional primary alcohol is prepared from a fluorinated diol B described above and a compound D containing at least two primary alcohol groups and one halo group suitable for ether formation. Examples of suitable compounds, D, include but are not limited to 2-(bromomethyl)-2-(hydroxymethyl)-1,3-propanediol, 2-(bromomethyl)-2-methyl-1,3-propanediol, 2-(bromomethyl)-2-ethyl-1,3-propanediol, 3-(bromomethyl)-3-methyl-1,5-pentanediol, 3-(bromomethyl)-3-(hydroxyethyl)-1,5-pentanediol. To avoid polymerization during the reaction it is preferred that the hydroxyl groups in D be protected before the reaction and then de-protected after the reaction.

In still another embodiment, the fluorinated multifunctional primary alcohol is prepared from a fluorinated dicarboxylic ester E and an amine, F, containing at least two primary hydroxyl groups. E and F react to form an amide.

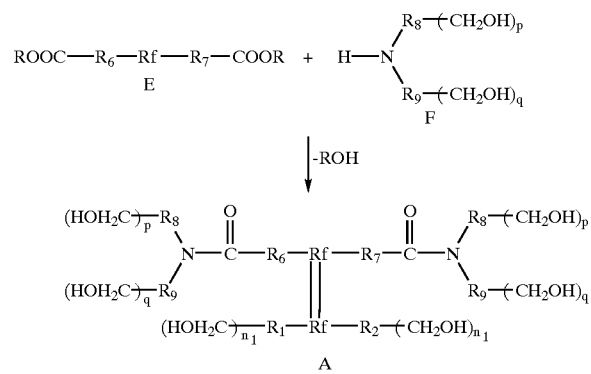

wherein Rf is a monomeric or polymeric perfluorinated alkylene, oxyalkylene, arylene, oxyarylene, and mixtures thereof; $R_6$ and $R_7$ are selected from the group consisting of difluoromethylene and other monomeric or polymeric divalent moieties such as alkylene, oxyalkylene, alkylene sulfide, arylene, oxyarylene, arylene sulfide, siloxane and mixtures thereof; $R_8$ and $R_9$ are radicals such as hydrogen, alkyl, alkylene, oxyalkylene, arylene, oxyarylene, and mixtures thereof; R is an alkyl radical such as methyl, ethyl and butyl; and p and q are integers, the sum of which is at least 2.

Non-exclusive examples of the fluorinated dicarboxylic ester E include dimethyl perfluroglutarate, dimethyl perfluoroadipate, dimethyl perflurosuberate, dimethyl perfluroazelate, dimethyl hexadecaflurosebacate, dimethyl tetracosafluro-1,10-decanedioate, and Fluorolink L and L10, available from Ausimont USA of Thorofare, N.J. Examples of suitable amines, F, include but are not limited to N,N-dihydroxyethylamine, N,N-dihydroxypropylamine, N,N-dihydroxybutylamine, serinol, 2-amino-2-ethyl-1,3-propanediol, 2-amino-2-methyl-1,3-propanediol, and tris (hydroxymethyl)-aminomethane.

Although only ester, ether and amide based syntheses are described other reactions known to those skilled in the art can be used for the preparation of the fluorinated multifunctional primary alcohols.

The primary alcohol of the present invention can be readily converted to other multifunctional compounds including, but not limited to acrylates, epoxies and vinyl ethers. In one embodiment, the fluorinated alcohol A is converted into an acrylate with acryloyl chloride using a tertiary amine. Preferably a hindered tertiary amine containing at least one tertiary or quaternary carbon atom is used. The hindered amine provides several advantages, as compared to commonly used triethylamine, such as reducing the yellowness of the products and eliminating the water washing process to remove ammonium salts formed during the acryloylation reaction. Non-exclusive examples of suitable hindered amines include N,N-dimethylisopropylamine, N,N-diisopropylethylamine, triisobutylamine, Julolidine, iminodibenzyl, 2-methylpyridine, 2,6-lutidine, 2,4,6-collidine, and mixtures thereof.

The acrylate discussed above has at least four acrylate groups per molecule. Such a molecule allows for fast curing and high crosslinking density and is suitable as a crosslinker in a coating composition containing fluorinated acrylates.

Although only the acrylate derivatives of the fluorinated multifunctional alcohol are described, other derivatives such as, but not limited to, epoxies and vinyl ethers can be synthesized from the same multifunctional alcohols using the skills well known to artisans.

The invention also provides a method of producing an optical coating comprising (1) forming a coating composition including at least one acrylate of this invention and at least one free radical initiator; (2) coating the composition into a film on a substrate having a substantially uniform thickness; and (3) curing the coating composition by exposure to an actinic radiation or heat, depending on the type of the initiator.

The coating composition is formed by thoroughly mixing the multifunctional acrylate of this invention with a free radical initiator and optionally other components such as, but not limited to, other acrylates and additives. The initiator can be either a photoinitiator, which generates free radicals when exposed to sufficient actinic radiation, or a thermal initiator, which generates free radicals when heated to a sufficient temperature. A composition containing a photo-initiator is herein called a photo-curable composition. A composition containing a thermal initiator is herein called a thermo-curable composition.

The photo-curable composition contains at least one photoinitiator having a weight percentage of 0.1–12%, preferably 0.2–6.0% and more preferably 0.5–2.0%. The photo-initiator is preferably thermally inactive below about 50° C. Examples of suitable photoinitiators include, but are not limited to, aromatic ketones, benzil ketals, benzoin, benzoin ethers, and phosphine oxides such as benzophenone, benzyl dimethyl ketal, benzoin alkyl ethers, 1-hydroxy-cyclohexyl-phenyl ketone, benzodimethyl ketal, α,α-dimethyloxy-α-hydroxy acetophenone, 1-[4-(2-hydroxyethoxy)phenyl]-2-hydroxy-2-methyl-propan-1-one, 2-methyl-1-[4-methylthio)phenyl]-2-morpholino-propan-1-one, 2-benzyl-2-dimethylamino-1-(4-morpholinophenyl)-butan-1-one, and 2,4,6-trimethylbenzoyldiphenylphosphine oxide, and mixtures thereof. The preferred photoinitiator composition is a mixture of at least two photoinitiators with different extinction coefficients and absorption maxima. Such mixed photoinitiator composition enables high photo contrast as well as fast curing speed. Examples of such mixtures include, but are not limited to, benzodimethyl ketal with α,α-dimethyloxy-α-hydroxy acetophenone and 2,4,6-trimethylbenzoyldiphenylphosphine oxide with α,α-dimethyloxy-α-hydroxy acetophenone.

The thermo-curable composition contains at least one thermal initiator at a weight percentage of 0.1–12%, preferably 0.2–6.0%, more preferably 0.5–2.0%. Suitable thermal polymerization initiators nonexclusively include peroxides such as benzoyl peroxide (BPO), di(sec-butyl) peroxydicarbonate, t-butyl peroxy-2-ethylhexanoate, t-butyl peroxyisobutyrate, 1,1-di-(amylperoxy)-cyclohexane, α-cumyl peroxyneodecanoate, t-amyl peroxyneodecanoate, laurolyl peroxide, dipropylperoxydicarbonate, decanoyl peroxide, cumene hydroperoxide, t-butyl cumyl peroxide, dicumyl peroxide, di-t-butyl peroxide, t-butyl hydroperoxide, di-t-butyl diperoxy-phthalate, t-amyl perbenzoate, t-butyl perbenzoate, t-butyl peroxyacetate, 2,5-dimethyl-2,5-di-(t-butylperoxy)hexane, 2,5-dihydroperoxy-2,5-dimethylhexane, t-amyl hydroperoxide, ethyl-3,3-di-(t-butylperoxy)-butyrate, 2,2-di-(t-butylperoxy)-butane and 2,2-di(t-amylperoxy)propane. Other suitable thermal initiators include alkyl azo compounds wherein the alkyl group contains from 1 to 20 carbon atoms, such as 2,2-azobis-2-methylpropionitrile; and mixtures thereof.

Optional additives may be added to the thermo-curable or photo-curable composition of this invention to enhance certain properties such as thermal stability, chemical stability, coating quality, and photo contrast. Examples of the additives include, but are not limited to, surfactants, contrast enhancers, photo stabilizers, UV absorbers, antioxidants, and dyes. Examples of surfactants include fluorinated surfactants such as Fluorad from 3M of St. Paul, Minn. and polyethers such as BYK-3500 from BYK Chemie USA of Wallingford, Conn. Suitable contrast enhancers include free radical scavengers particularly photo bleachable free radical scavengers such as the nitrones reported in U.S. Pat. No. 6,162,579. Photo stabilizers include hindered amines such as Cyasorb UV3346 from Cytec Industries of West Paterson, N.J. and TINUVIN 123S from Ciba Specialty Chemicals of Tarrytown, N.Y. UV absorbers include benzotriazoles such as TINUVIN 234 from Ciba Specialty Chemicals and benzophenone derivatives such as UVINUL from BASF of Mount Olive, N.J. Antioxidants include for example hindered phenols such as Irganox 1010 from Ciba Specialty Chemicals. Dyes include methylene green, methylene blue and the like.

The resulting composition may be coated on a variety of substrates using methods well known in the art, including, but not limited to, spin coating, slot coating, dip coating, and spray coating. Suitable substrates include, but are not limited to, silicon, glass, quartz, plastic, and metal. The coating is cured by exposure to sufficient actinic radiation or heat. The polymer coating demonstrates high cross-linking density, high optical clarity, low birefringence, good thermal stability, low glass transition temperature, and good adhesion to the substrates.

The actinic radiation used can be any light in the visible and ultraviolet regions of the spectrum as well as electron beam. Preferably the actinic radiation is UV light. The UV sources, wavelengths, intensity, and exposure procedures may be varied to achieve the desired curing degree. Useful UV sources are high pressure xenon or mercury-xenon arc lamps.

This invention further provides a waveguide device formed by patterning the optical coating composition of the present invention. The coating can be patterned with a variety of methods known to those skilled in the art such as, but not limited to, reactive ion etching and photolithography. The waveguides fabricated using the fluorinated polymers exhibit low optical loss at telecom wavelengths from 1300 to 1600 nm.

EXAMPLES

The following non-limiting examples are given only for the purpose of illustrating this invention. Variations in composition and synthetic methods will be apparent to those skilled in the art and are considered within the scope of this invention.

Example 1.

Protection of Hydroxyl Groups

To a round-bottom flask equipped with a magnetic stirring bar was charged 2,2-bis(hydroxymethyl)-propionic acid (40 grams), dimethoxypropane (45 ml), pyridinium p-toluenesulfonate (3.75 g), and acetone (150 ml). The mixture was stirred at room temperature and the progress of the reaction was monitored by FT-IR. After the reaction was complete the reaction mixture was diluted with 650 ml of ether. Pyridinium p-toluenesulfonate precipitated and was removed by filtration. The ether solution was washed three times with 200 ml of saturated NaCl aqueous solution and dried over $MgSO_4$. The solvent was removed with a rotary evaporator to result in 49.4 g of isopropylidene-2,2-bis(methoxymethyl)-propionic acid.

Example 2.

Esterification of Fluorinated Alcohol

The isopropylidene-2,2-bis(methoxymethyl)-propionic acid prepared in Example 1 (38.3 g), Fluorolink D10, available from Ausimont USA (100 g), and 4-N,N-dimethyl-pyridine (1.22 g) were dissolved in 550 ml of dry mixture of methylene chloride and trichloro-trifluoroethane in a three-necked round-bottom flask. The mixture was cooled to 0° C. Dicyclohexylcarbodiimide (45.4 g) was dissolved in 140 ml of methylene chloride and added dropwise into the reaction mixture through an additional funnel. The mixture was stirred at 0° C. for an hour and then at room temperature for 18 hours. After the reaction was complete the white precipitate formed was filtered. The filtrate was concentrated and then purified by column chromatography to afford 87 g of fluorinated ester product.

Example 3.

Deprotection of Hydroxyl Groups

The fluorinated ester prepared in Example 2 (87 g), pyridinium p-toluenesulfonate (1.6 g), methanol (250 ml) and trichloro-trifluoroethane (150 ml) were mixed in a round-bottom flask equipped with a magnetic stirring bar. The mixture was heated to reflux and the progress of the reaction was followed by NMR. After the reaction was complete, the solvent was removed using a rotary evaporator and pyridinium p-toluenesulfonate was precipitated with ether. The fully de-protected fluorinated tetra-alcohol was obtained by column chromatography with 72% yield.

Example 4.

Preparation of Fluorinated Acrylate

The fluorinated tetra-alcohol prepared in Example 3 (55 g) and hydroquinone (200 ppm) were mixed with 100 ml of anhydrous ether in an argon-protected three-necked flask. To the reaction mixture was added 20.5 ml of acryloyl chloride. Anhydrous diisopropylethylamine (43.6 ml) was added dropwise under agitation. The reaction mixture was stirred for an additional 6 h at room temperature. The reaction mixture was then quenched with 2 ml of methanol and stirred for 2 h to consume excess acryloyl chloride. Finally the mixture was filtered through Celite/silica to remove salt, and the filtrate solution was concentrated and pumped under vacuum at 60° C. to yield a fluorinated tetraacrylate.

Example 5.

Preparation of Tetrahydroxyl Fluorinated Amide

Fluorolink L-10 (methyl ester of a fluorinated acid, 50 g), available from Ausimont USA, was added into a three-necked round-bottom flask equipped with a magnetic stir-ring bar. Diethanolamine (11.7 grams) was added dropwise to the flask through an additional funnel. The reaction mixture was stirred at room temperature for 2 hours and the progress of the reaction was monitored by FT-IR. Once the reaction was complete, the crude product was diluted with 200 ml of ether. The ether solution was washed with 30 ml of 0.5 M HCl aqueous solution and subsequently saturated NaCl aqueous solution. The resulting ether solution was dried over $MgSO_4$ and the solvent was removed with a rotary evaporator. The tetrahydroxyl fluorinated amide obtained was a colorless and viscous oil (47.2 g).

Example 6.

Preparation of Fluorinated Tetraacrylate

The tetraalcohol prepared in Example 5 (47.24 g) and hydroquinone (10 mg) were mixed with 100 ml of anhydrous ether in an argon-protected three-necked flask. To the reaction mixture was added 14.8 ml of acryloyl chloride. Anhydrous diisopropylethylamine (31.6 ml) was then added dropwise under agitation. The reaction mixture was stirred for an additional 6 h at room temperature. The reaction mixture was quenched with 1 ml of methanol and stirred for 2 h to consume excess acryloyl chloride. Finally the mixture was filtered through Celite/silica to remove salt, and the filtrate solution was concentrated and pumped under vacuum at 60° C. to yield a fluorinated liquid tetraacrylate.

Example 7.

Formation of Optical Coating

The tetraacrylate of Example 4 was mixed with 1% Darocur 1173, a free radical photoinitiator from Ciba Specialty Chemicals, to form a photosensitive composition. The photosensitive composition was coated on a glass substrate and exposed to 500 mJ UV at 365 nm using an 800W mercury xenon lamp to form a thin polymer coating. The coating was clear and colorless.

Example 8.

Formation of Optical Coating

The acrylate of Example 6 was mixed with 0.5% benzoyl peroxide (BPO), a free radical initiator, to form a thermo-curable composition. The composition was coated on a silicon substrate and heated at 90° C. for 2 h to form a thin solid film. The coating was clear and colorless.

Although the present invention has been shown and described with respect to several preferred embodiments thereof, various changes, omissions and additions to the form and detail thereof, may be made therein, without departing from the spirit and scope of the invention.

What is claimed is:

1. A multifunctional alcohol having the following formula:

$$(HOH_2C)_{\overline{n_1}}R_1\text{-Rf-}R_2\text{-}(CH_2OH)_{n_1}$$

wherein Rf is a monomeric or polymeric perfluorinated oxyalkylene; $R_1$ and $R_2$ are monomeric or polymeric multivalent radicals selected from a group consisting of aliphatic esters, aliphatic amides, and mixtures thereof; and $n_1$ is an an integer of at least 2.

2. The multifunctional alcohol of claim 1 wherein Rf has a molecular weight of at least 25% of the molecular weight of the alcohol.

3. The multifunctional alcohol of claim 1 wherein Rf is selected from the group containing the following structures:

$$-(CF_2O)_m-$$

$$-CF_2O(CF_2CF_2O)_nCF_2-$$

$$-CF_2CF_2O(CF_2CF_2CF_2O)_nCF_2CF_2-$$

$$-CF_2CF_2CF_2O(CF_2CF_2CF_2CF_2O)_nCF_2CF_2CF_2-$$

$$CF_2O(CF_2CF_2O)_n(CF_2O)_m-$$

$$CF_2O(CF_2CF_2O)_m(CF_2CF_2CF_2CF_2O)_n(CF_2CF_2O)_mCF_2-$$

and $$CF_2O(CF_2CF_2O)_m(CF_2CF_2CF_2O)_nCF_2CF_2O-(CF_2CF_2CF_2O)_n(CF_2CF_2O)_mCF_2,$$

wherein
Rf has a molecular weight of at least 25% of the molecular weight of the alcohol and wherein each m and n is an integer.

4. The multifunctional alcohol of claim 1 wherein each $R_1$ and $R_2$ contains at least 1 ester group.

5. The multifunctional alcohol of claim 4 having the structure of:

$$HOH_2C-\underset{\underset{HOH_2C}{|}}{\overset{\overset{CH_3}{|}}{C}}-\overset{\overset{O}{\|}}{C}-OCH_2-Rf-CH_2O-\overset{\overset{O}{\|}}{C}-\underset{\underset{CH_2OH}{|}}{\overset{\overset{CH_3}{|}}{C}}-CH_2OH$$

wherein Rf is a monomeric or polymeric perfluorinated oxyalkylene.

6. The multifunctional alcohol of claim 1 wherein each $R_1$ and $R_2$ contains at least 1 amide group.

7. The multifunctional alcohol of claim 6 having the structure of:

$$\underset{HOH_2CH_2C}{\overset{HOH_2CH_2C}{\diagdown}}N-\overset{\overset{O}{\|}}{C}-Rf-\overset{\overset{O}{\|}}{C}-N\underset{CH_2CH_2OH}{\overset{CH_2CH_2OH}{\diagup}}$$

wherein Rf is a monomeric or polymeric perfluorinated oxyalkylene.

8. A fluorinated multifunctional crosslinker having the structure of:

$$(ZOH_2C)_{n_2}-R_1-Rf-R_2-(CH_2OZ)_{n_2}$$

wherein Rf is a monomeric or polymeric perfluorinated oxyalkylene $R_1$ and $R_2$ are monomeric or polymeric multivalent radicals selected from a group consisting of aliphatic esters, aliphatic amides, and mixtures thereof; Z is selected from the group consisting of acrylate, epoxy and vinyl ether functional groups; and $n_2$ is an integer of at least 2.

9. The fluorinated multifunctional crosslinker of claim 8 wherein Rf has a molecular weight of at least 25% of the molecular weight of the crosslinker molecule.

10. A fluorinated multifunctional acrylate prepared from the fluorinated multifunctional alcohol of claim 1 having at least 3 acrylate groups.

11. A fluorinated multifunctional acrylate having the structure of:

$$(H_2C=HCCOOH_2C)_{n_3}-R_1-Rf-R_2-(CH_2OOCCH=CH_2)_{n_3}$$

wherein Rf is a monomeric or polymeric perfluorinated oxyalkylene $R_1$ and $R_2$ are monomeric or polymeric multivalent radicals selected from a group consisting of aliphatic esters, aliphatic amides, and mixtures thereof; and $n_3$ is an integer of at least 2.

12. The multifunctional acrylate of claim 11 wherein Rf has a molecular weight of at least 25% of the molecular weight of the acrylate.

13. The multifunctional acrylate of claim 11 wherein Rf is selected from the group containing the following structures:

$$-(CF_2O)_m-$$

$$-CF_2O(CF_2CF_2O)_nCF_2-$$

$$-CF_2CF_2O(CF_2CF_2CF_2O)_nCF_2CF_2-$$

$$-CF_2CF_2CF_2O(CF_2CF_2CF_2CF_2O)_nCF_2CF_2CF_2-$$

$$CF_2O(CF_2CF_2O)_n(CF_2O)_m-$$

$$CF_2O(CF_2CF_2O)_m(CF_2CF_2CF_2CF_2O)_n(CF_2CF_2O)_mCF_2-$$

and $$CF_2O(CF_2CF_2O)_m(CF_2CF_2CF_2O)_nCF_2CF_2O-(CF_2CF_2CF_2O)_n(CF_2CF_2O)_mCF_2-$$

wherein Rf has a molecular weight of at least 25% of the molecular weight of the alcohol and wherein each m and n is an integer.

14. The multifunctional acrylate of claim 11 having the structure of:

$$H_2C=HCCOOH_2C-\underset{\underset{H_2C=HCCOOH_2C}{|}}{\overset{\overset{CH_3}{|}}{C}}-\overset{\overset{O}{\|}}{C}-OCH_2-Rf-CH_2O-\overset{\overset{O}{\|}}{C}-\underset{\underset{CH_2OOCCH=CH_2}{|}}{\overset{\overset{CH_3}{|}}{C}}-CH_2OOCCH=CH_2$$

wherein Rf is a monomeric or polymeric perfluorinated oxyalkylene.

15. The multifunctional acrylate of claim 11 having the structure of:

$$\underset{H_2C=HCCOOH_2C}{\overset{H_2C=HCCOOH_2C}{\diagdown}}N-\overset{\overset{O}{\|}}{C}-Rf-\overset{\overset{O}{\|}}{C}-N\underset{CH_2OOCCH=CH_2}{\overset{CH_2OOCCH=CH_2}{\diagup}}$$

wherein Rf is a monomeric or polymeric perfluorinated oxyalkylene.

16. A coating composition comprising:
   a) at least one multifunctional acrylate having the structure of $$(H_2C=HCCOOH_2C)_{n_3}-R_1-Rf-R_2-(CH_2OOCCH=CH_2)_{n_3}$$

wherein Rf is a monomeric or polymeric perfluorinated oxyalkylene $R_1$ and $R_2$ are monomeric or polymeric multivalent radicals selected from a group consisting of aliphatic esters, aliphatic amides, and mixtures thereof; and $n_3$ is an integer of at least 2; and b) at least one free radical initiator.

17. The coating composition of claim 16 wherein the free radical initiator is a photoinitiator which generates free radicals upon exposure to sufficient actinic radiation.

18. A waveguide device formed by patterning a coating composition comprising:

a) at least one multifunctional acrylate having the structure of:

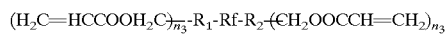

wherein Rf is a monomeric or polymeric perfluorinated oxyalkylene; $R_1$ and $R_2$ are monomeric or polymeric multivalent radicals selected from a group consisting of aliphatic esters, aliphatic amides, and mixtures thereof; and $n_3$ is an integer of at least 2; and b) at least one free radical initiator.

19. The waveguide device of claim 17 wherein the free radical initiator is a photoinitiator which generates free radicals upon exposure to sufficient actinic radiation.

* * * * *